United States Patent
Weston et al.

(10) Patent No.: US 6,216,493 B1
(45) Date of Patent: Apr. 17, 2001

(54) METHOD AND APPARATUS FOR MAKING AN ARTICLE FROM A FORMABLE MATERIAL

(75) Inventors: Terence Edward Weston, Eye; Christopher John Briggs, Haverhill, both of (GB)

(73) Assignee: Weston Medical Limited, Suffolk (GB)

( * ) Notice: Subject to any disclaimer, the term of this patent is extended or adjusted under 35 U.S.C. 154(b) by 0 days.

(21) Appl. No.: 09/285,190

(22) Filed: Mar. 24, 1999

Related U.S. Application Data

(63) Continuation of application No. PCT/GB97/02560, filed on Sep. 22, 1997.

(30) Foreign Application Priority Data

Sep. 25, 1996 (GB) ................................................. 9620173
Nov. 29, 1996 (GB) ................................................. 9624870

(51) Int. Cl.[7] ................................................. C03B 23/09
(52) U.S. Cl. .................. 65/68; 65/36; 65/56; 65/57; 65/102; 65/112; 65/105; 65/108; 65/109; 65/166; 65/177; 65/292; 65/296; 425/392; 425/393; 264/154; 264/238; 264/255; 264/259; 264/267; 264/319; 264/299; 264/325
(58) Field of Search .................... 65/36, 56, 57, 65/68, 102, 111, 105, 108, 109, 166, 177, 292, 296; 425/392, 393; 264/154, 238, 255, 259, 267, 319, 299, 325

(56) References Cited

U.S. PATENT DOCUMENTS

| | | | |
|---|---|---|---|
| 1,999,525 | * 4/1935 | Morscholz | ............................. 65/109 |
| 2,392,104 | * 1/1946 | Smith . | |
| 2,403,042 | * 7/1946 | Bogoslowsky . | |
| 2,736,992 | * 3/1956 | Magash et al. | ........................ 65/108 |
| 2,788,544 | * 4/1957 | Voumard et al. . | |
| 2,958,898 | * 11/1960 | Voumard et al. . | |
| 3,237,243 | 3/1966 | Saumsiegle et al. | ...................... 18/5 |
| 3,280,423 | * 10/1966 | Voumard . | |
| 4,254,075 | * 3/1981 | Menzel et al. . | |
| 4,623,117 | * 11/1986 | Ueberegger . | |

FOREIGN PATENT DOCUMENTS

| | | |
|---|---|---|
| 525515 | 5/1931 | (DE) . |
| 2361217 | 3/1978 | (FR) . |
| 880666 | 10/1961 | (GB) . |
| 93/23225 | 11/1993 | (WO) . |

* cited by examiner

*Primary Examiner*—James Derrington
*Assistant Examiner*—Michael P. Colaianni
(74) *Attorney, Agent, or Firm*—Darby & Darby

(57) ABSTRACT

A method and apparatus are described for making an article such as the body of a needleless injector capsule, from a formable material, such as glass, the article having a cavity communicating with the exterior via an orifice. A blank (1*a*) having an open end is mounted on a first forming tool, and the open end is engaged by a second forming tool (22) while an end region of the blank (1*a*) adjacent the open end is in a condition to permit it to be formed. One of the tools (7*a*) has a pin (21) extending therefrom, and when the tools are brought together to form the end region into the desired shape of the pin (21) defines the orifice.

29 Claims, 5 Drawing Sheets

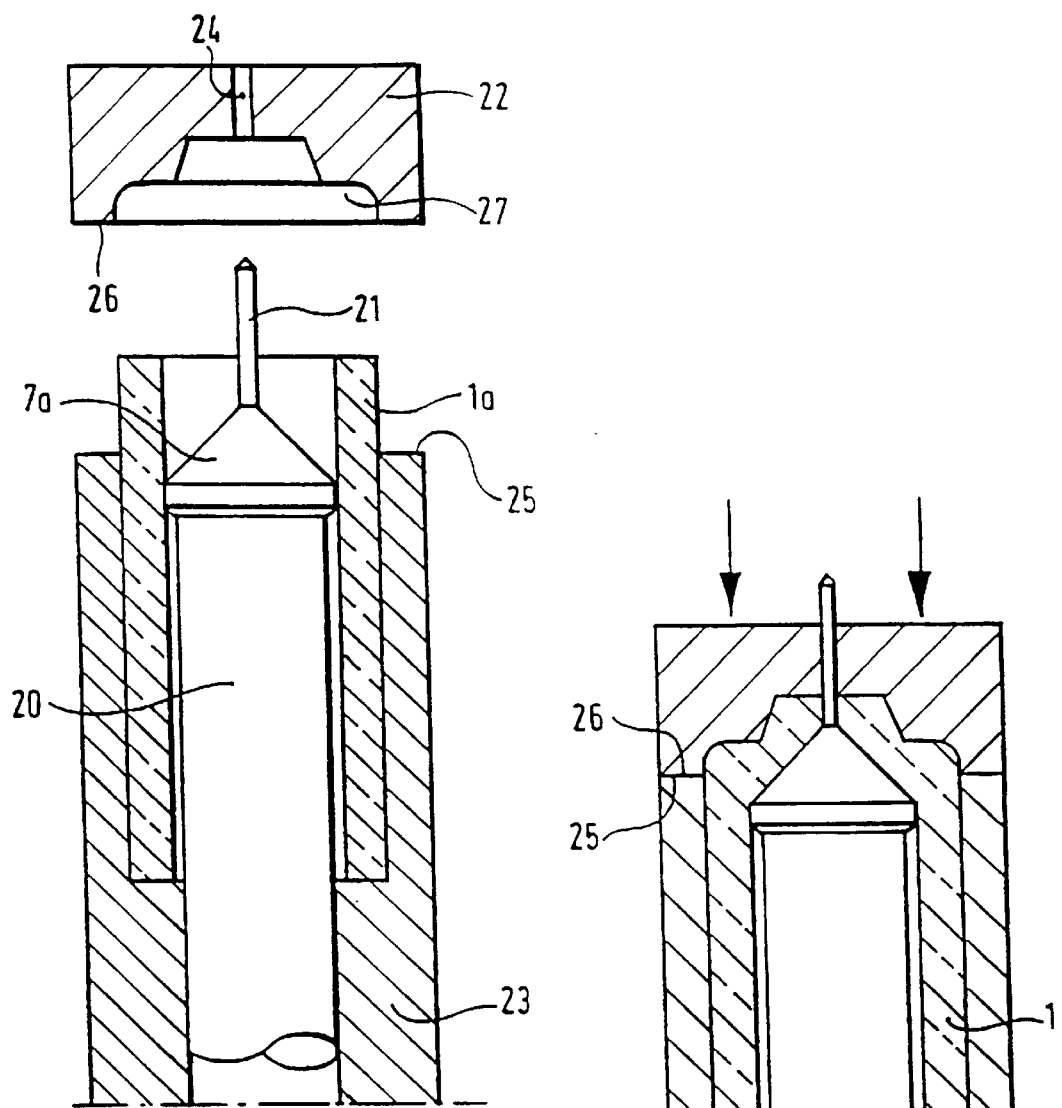

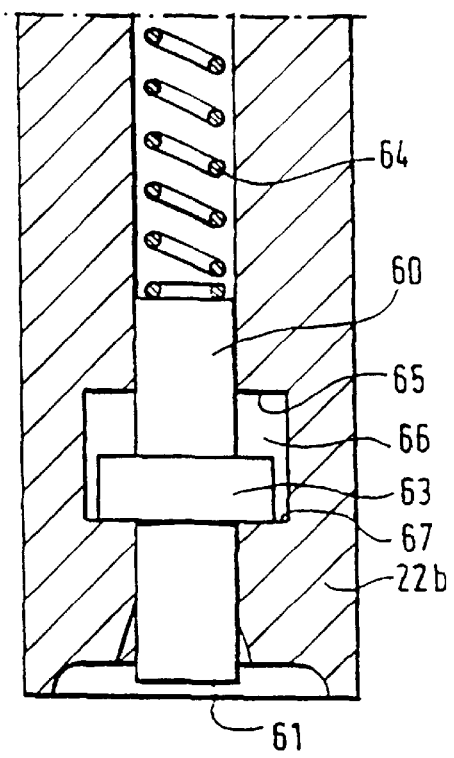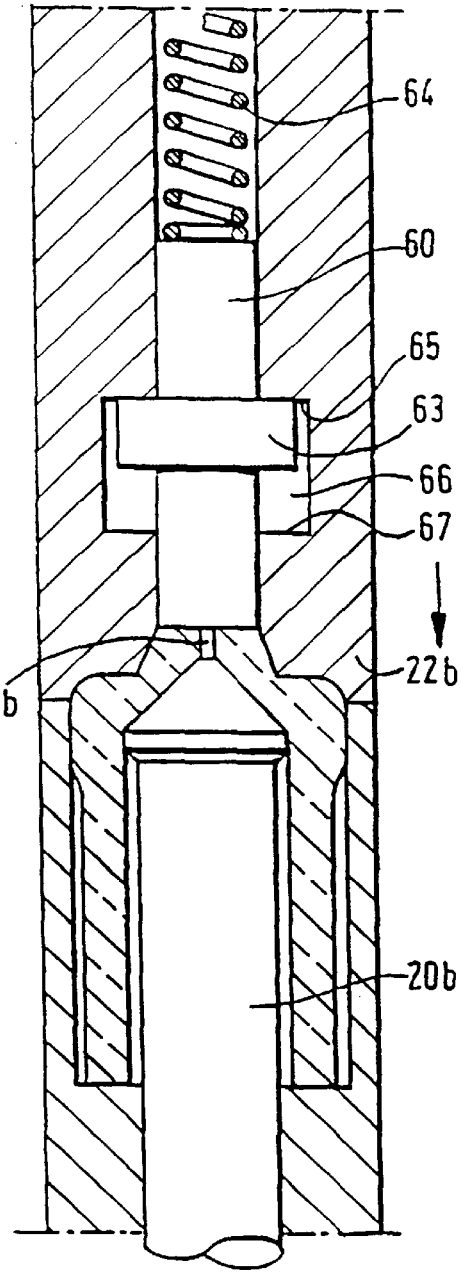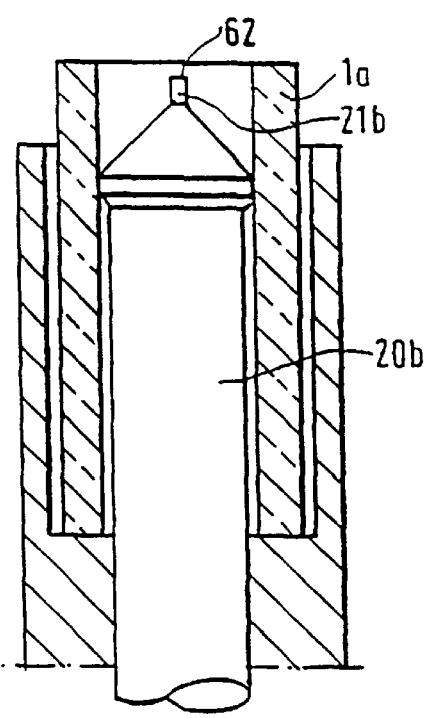
FIG.7a. FIG.7b.

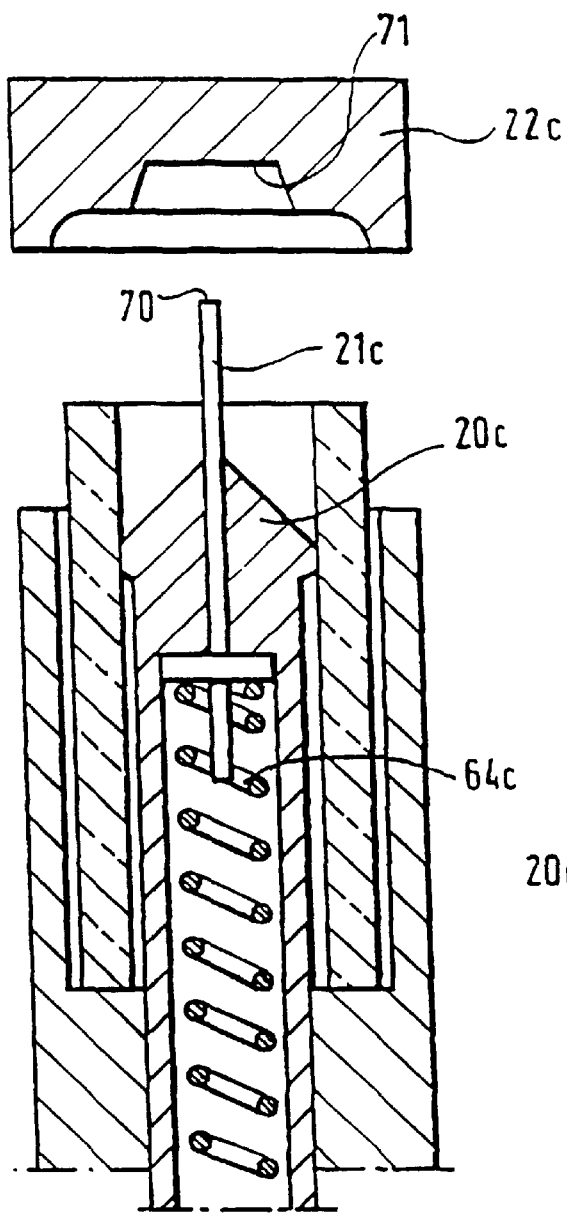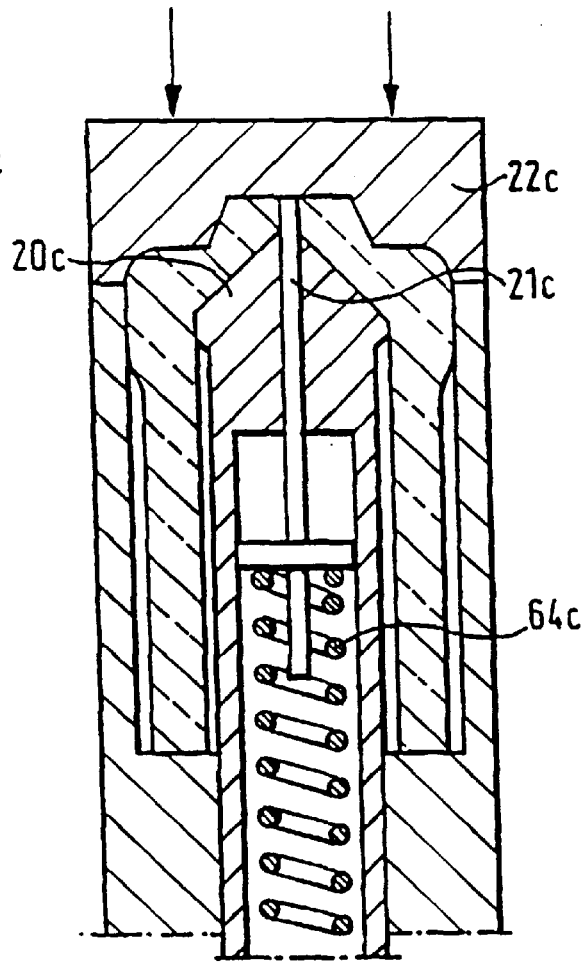
FIG.8a.
FIG.8b.

METHOD AND APPARATUS FOR MAKING AN ARTICLE FROM A FORMABLE MATERIAL

This is a continuation of International Application No. PCT/GB97/02560 filed Sep. 22, 1997 (now expired), the entire disclosure of which is hereby incorporated by reference.

FIELD OF THE INVENTION

The invention is in the field of needleless injectors which use a capsule for containing a liquid drug to be injected, and needle-type hypodermic syringe bodies.

BACKGROUND OF THE INVENTION

Needleless injectors are used as an alternative to conventional hypodermic injectors to deliver medicaments through the patient's skin into the underlying tissues. Such injectors use a high pressure piston pump to dispense a jet of liquid drug with sufficient force to penetrate the skin, and thereafter deposit the drug into the dermal, subcutaneous or muscular tissues.

The drug is dispensed from a cylindrical chamber, having a fine orifice at one end through which the drug is discharged. A piston is slidingly and sealingly located in the chamber, and the drug is contained within the space between the orifice and piston. To make an injection, the orifice is placed on the skin, and by operating a release mechanism, the piston is acted upon by a force which may be derived from a spring, pressurised gas or chemical reaction.

The capsule may be filled by the user, or may be prefilled and pre-assembled to an actuator. In the latter case particularly, the materials from which the capsule and piston are constructed must be inert to the drug—i.e. they must not react with the drug chemically, nor physically, and must not contain harmful extractives that might contaminate the drug. The choice of materials is small: borosilicate glass is the most favoured capsule material when drugs must be stored for more than a few hours. If an alternative material is selected for the capsule, years of testing must be done to validate that material, whereas borosilicate glass has a known compatibility with most drugs.

During the injection, the pressure generated in the capsule is at least 100 bars, and it is preferable, in order to avoid leakage during injection, that the orifice is integral with the cylindrical chamber. Furthermore, the form and dimension of the orifice is critical to the injection performance, and for repeatable results these features should be made to close tolerances. However, glass is a difficult material to mould and maintain such close tolerances over many millions of components. One traditional method is to work the heated and softened end of a glass tube on a lathe, and by applying a shaping wheel or paddle, to close up one end onto a mandrel to form the orifice. This is a relatively crude method, and the only parameters that may be controlled accurately are the orifice diameter and the diameter of the surrounding glass: the length and entry profile of the orifice are left to chance because the process shapes only the outside of the tube and the orifice diameter. An alternative process is moulding, whereby a hot "gob" of molten glass is moulded in a die. This process is suitable for large components, but needleless injector capsules are seldom larger than 1 ml capacity, and such a small gob of glass loses its heat rapidly and is difficult to mould. Also the surface finish inside a moulded tube is not smooth enough for this application, nor is the bore parallel. Drawn tubing, which has an excellent surface finish and form, is the preferred starting material, but current working methods, as described, do not provide control of both inside and outside dimensions.

Conventional glass hypodermic syringes are made on automatic lathes from glass by working heat-softened tube, as previously described. Low cost disposable glass syringes are generally made with the hollow needle glued into a precisely formed hole in one end of the syringe body. The manufacturing process is relatively primitive, with low production rates and high reject rates.

OBJECT OF THE INVENTION

The present invention seeks to overcome the drawbacks of current glass tube forming methods by providing a means of forming the orifice, and the inside and outside profiles of a needleless injector capsule or hypodermic syringe body, which means has excellent repeatability and is capable of high speed production.

SUMMARY OF THE INVENTION

According to the invention there is provided a method of making an article from a formable material, the article having a cavity communicating with the exterior via an orifice, wherein a blank having an open end is mounted on a first forming tool, and the open end is engaged by a second forming tool while an end region of the blank adjacent the said open end is in a condition to permit it to be formed, one of the said tools having a pin extending therefrom, and the said one tool and the other of said tools are brought together to form the said end region into a desired shape, with the pin defining the said orifice.

The invention further provides an apparatus for making an article from a formable material, the article having a cavity communicating with the exterior via an orifice, comprising a first forming tool for receiving an open-ended blank, and a second forming tool for engaging an end region of the blank adjacent the open end thereof to form the same, one of the said tools having a pin extending therefrom, the tools being so arranged that when they are brought together to form the said end region into a desired shape the pin defines the said orifice.

The pin can be on either of the forming tools, though in the embodiments described below it is preferably on the first forming tool.

In a preferred embodiment of the invention, a glass tube, cut to length, is placed onto a mandrel having a profile to which the glass may be formed. The mandrel has a pin at its extreme for forming the orifice. The glass is rotated and heated on the end to be formed. When it is at the optimum forming consistency, a form tool having a profile to which the outside of the tube is to be formed, is applied to the exterior of the glass tube and presses the softened glass onto the mandrel and pin. Immediately before forming, the rotation of the glass tube is stopped; alternatively the external forming tool is rotated at the same speed as the tube, so that there is no relative movement between the tube and external form tool.

BRIEF DESCRIPTION OF THE DRAWINGS

A detailed description of the invention will now follow, with reference to the accompanying drawings, in which:

FIG. 2 shows a glass tube placed on a mandrel, with external form tool adjacent;

FIG. 3 depicts the form tools in position having pressed the glass into the required shape;

FIGS. 7a and 7b show a further modified method of forming a capsule; and

FIGS. 8a and 8b show yet another modified method of forming a capsule.

DETAILED DESCRIPTION OF THE INVENTION

Figure 1:
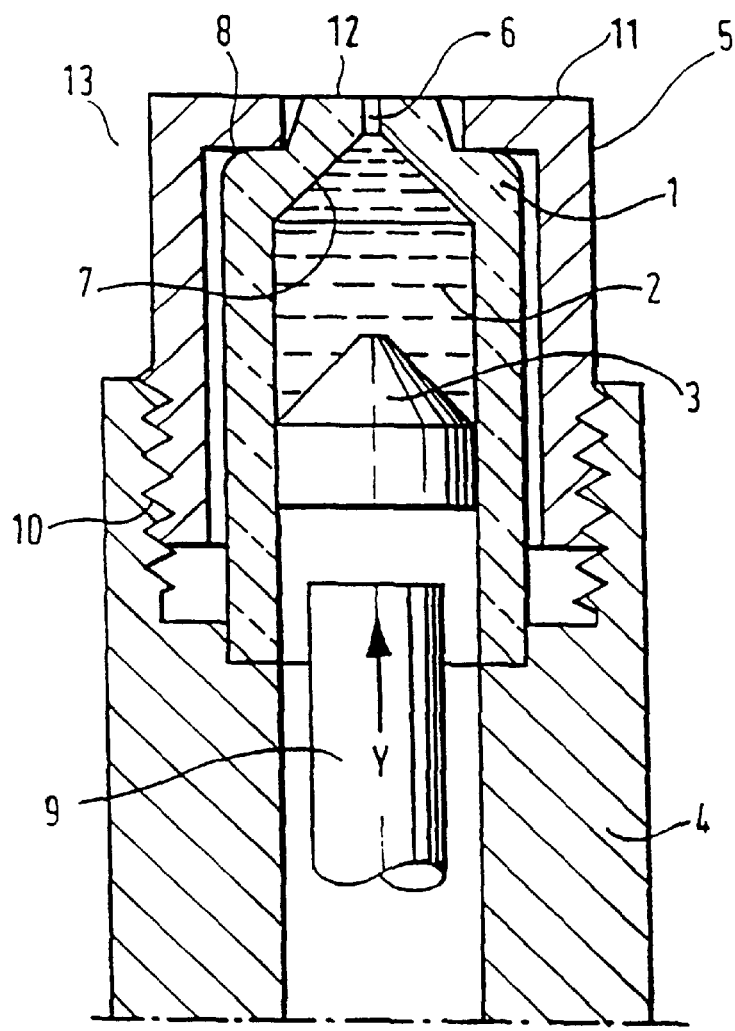
FIG. 1 shows a centreline section through a typical glass capsule, assembled to the nose of an actuator or power source.

Referring first to FIG. 1, capsule 1 is a cylinder containing drug 2, and a piston 3 in contact with drug 2. The capsule 1 is retained in the nose 4 of a needleless injector actuator by retaining cap 5 bearing on shoulder 8 of the capsule 1. Cap 5 may be retained by screw threads 10, snap means or other suitable device. The discharge end of the interior of capsule 1 is characterised by a frusto-conical form 7 leading into the orifice 6. When the injector is operated, a ram 9 biassed in direction Y is released so as to engage and drive the piston 3 to discharge the drug 2 through orifice 6.

The ratio of the orifice length to diameter should be as small as practicable, and it is desirable that this should be no more than 2:1. This ratio has a significant effect on the flow resistance of the orifice: too high and the orifice resembles a tube with a corresponding increase in flow resistance. Typically, the orifice diameter may be within the range of 0.1 mm to 0.5 mm, with corresponding lengths within the range of 0.2 mm to 1.0 mm.

When performing an injection, the face 11 of the retainer 5 is pressed lightly on the patient's skin, and the area of face 11 provides sufficient support to prevent the injector capsule assembly sinking into the tissues. If the face 12 is flush or slightly behind face 11, the orifice is in very light contact with the skin, and an intradermal injection will result; a firm contact—i.e. face 12 protrudes slightly from face 11—will result in a subcutaneous injection; and if face 12 protrudes considerably from face 11 thereby displacing and compressing adipose tissue, then the injection may be intramuscular. This is, of course, a generalisation, since other factors such as pressure and orifice size may be adjusted to achieve the required injection characteristics. Nevertheless, the relationship of the capsule face and retainer face must be controlled to achieve repeatable high quality injections.

The purpose of the frusto-conical form 7 which joins the cylindrical section of capsule 1 to the orifice 6 is to reduce turbulent energy losses as the drug is forced into the orifice 6, and also to minimise during injection the stresses within the glass walls of capsule 1 as the cylindrical bore reduces to the orifice 6.

The foregoing description covers the essential design requirements of a needleless injector capsule: there may be small variations but the great majority of injectors use a capsule having a form similar to that described.

Referring now to FIG. 2, the material for the capsule 1 is a length of glass tube 1a, which is located over mandrel 20 and rests on tube support 23. The mandrel 20 has a frusto-conical form 7a, terminating in a pin 21. Located concentrically above the mandrel 20 is a form tool 22, which has a forming surface 27. A hole 24 in the form tool 22 is a close clearance fit relative to pin 21.

The forming process commences by heating the tube 1a in the area of the frusto-conical section 7a of mandrel 20 to a temperature sufficient to soften the glass. Preferably, at least the mandrel 20 is rotated, (and more preferably the tube support 23 and mandrel 20 are rotated in unison, i.e. at the same speed and in the same direction), together with the glass tube 1a, during heating, so that the temperature of the glass is evenly distributed. Alternatively, the parts may remain stationary, the glass being heated by a ring burner. When the optimum temperature is reached, the form tool 22 is pressed onto the softened glass as shown in FIG. 3, and thus shapes the glass tube 1a to form the capsule 1. This is done either with the support 23 and mandrel rotating in unison, or with both stationary. The lengths of the orifice 6 and other features are controlled by the face 26 of the form tool 22 abutting face 25 of tube support 23, but other stop means may be equally effective.

Figure 4:
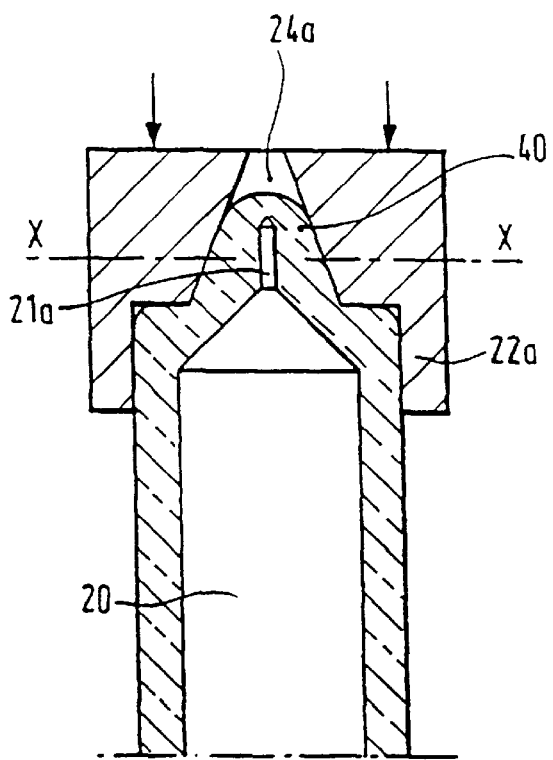
FIGS. 4 and 5 show modified forming methods that will accommodate wide tolerance glass tube.

The process described and illustrated by FIGS. 2 and 3 is idealised and would require an exact volume of glass tubing to be presented to the form tool. In practice, the dimensional tolerances of glass tube are quite large, and even if an accurate bore tubing is specified, the variation in wall thickness results in a wide variation in the outside diameter. FIG. 4 shows a method of overcoming this problem. The form tool 22a has a hole 24a which is substantially larger in cross-section than the corresponding pin 21a. This pin is shorter than the pin shown in FIG. 2. In the illustration, hole 24a is frusto-conical, and has a substantially larger cross-section than the pin 21a at least for that length of the hole over which the pin extends. In other words, there is a substantial clearance between the pin and the surface defining the hole. The glass tube is cut so that the volume is slightly greater than required for the finished capsule, and during forming, any excess material is forced along hole 24a to form a blob 40, whereby the hole formed by pin 21a is closed. After removing the formed tube from the mandrel and tube support, the blob 40 is cut at X—X and the cut face is flame polished to remove sharp edges and to smooth out any surface roughness. If necessary, after cutting, the face may be ground before flame polishing.

Figure 5:
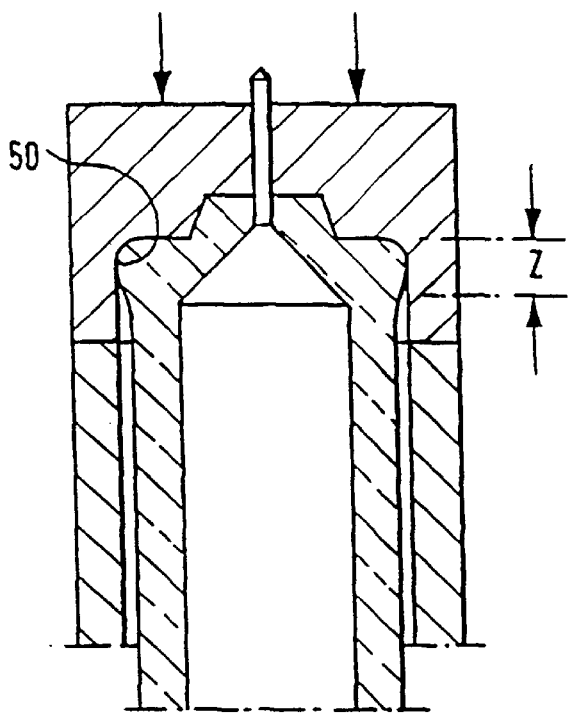

FIG. 5 shows another method of dealing with excess material. Again, the volume of the glass tube is slightly more than the finished capsule, and during forming, the excess glass is allowed to spread into the form tool to make a rim 50, the length Z of which may vary according to the amount of excess glass. This method has the additional advantage that the diameter of the rim 50 is controlled, regardless of the wall thickness tolerance.

It is important that the orifice is formed without any glass "flash", and whilst FIGS. 3 and 5 show pin 21 entered into hole 24, the annular clearance between pin and hole must be very small to prevent the ingress of molten glass which would form a thin skin or "flash" across the orifice 6. As a result, the alignment of the forming tool and mandrel is critical in FIGS. 3 and 5 to ensure that the pin 21 enters hole 24 without bending or jamming. This requires accurate and costly tools.

FIGS. 7a and 7b show a method of preventing flash formation around the orifice without the necessity of very accurate tool alignment. Plunger 60 is a sliding fit within forming tool 22b and a compression spring 64 bears on plunger 60 which carries a collar 63 fixed thereto. The total sliding movement permitted is controlled by the faces of the collar 63 and abutment faces 65 and 67 within a cavity 66 in the forming tool 22b. The mandrel 20b carries a pin 21b which has a flat distal face 62, and plunger 60 has a flat distal face 61. When the glass is formed, substantially as already described, the faces 61 and 62 cooperate to form a tight "shut-off" to prevent molten glass forming a thin skin over the end of the orifice in the capsule. The force of the shut-off is determined by the spring 64.

FIGS. 8a and 8b show a similar arrangement, but in this case the pin 21c is spring loaded by a compression spring 64c and slides in mandrel 20c. When the forming tool 22c and the mandrel 20c are brought together to form the glass, a face 70 of pin 21c cooperates with a face 71 of the forming tool 22c to form a tight shut-off.

Figure 6:
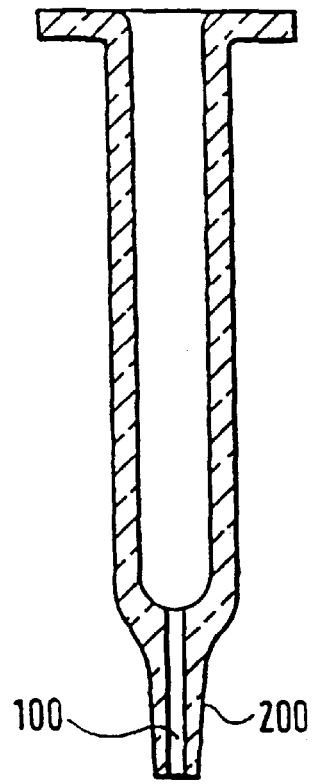
FIG. 6 shows a hypodermic syringe body.

The foregoing methods of forming the glass tube may be applied with equal efficacy to the production of glass syringes, as shown in FIG. 6. In this case, the diameter of hole 100 may be required to be closely controlled to accept a hollow needle: the needle may be bonded into the glass with a minimum thickness of adhesive. Alternatively, the frusto-conical tip 200 may be dimensioned to accept a so-called Luer-fitting needle, i.e. a needle with an adaptor having a co-operating internal taper by which means the needle may be frictionally retained on the syringe tip.

The method of forming tubing to make needleless injector capsules and hypodermic syringes may be applied to materials other than glass where conventional forming methods are inappropriate.

What is claimed is:

1. A method of making an article from a formable material, using a forming apparatus having an inner forming tool and an outer forming tool, the article having a cavity communicating with the exterior via an orifice, wherein a blank having an open end is mounted on the inner forming tool, and the open end is engaged by the outer forming tool while an end region of the blank adjacent the said open end is in a condition to permit it to be formed, a first one of the said tools having a pin extending therefrom, a second one of said tools comprising an other tool, said tools being brought together to form the said end region into a desired shape, in which the inner surface of the said end region conforms to the adjacent surface of the inner forming tool, with the pin defining the said orifice, the other forming tool having a cavity therein, facing the inner forming tool, of larger cross-section than the blank and extending beyond the outside of the blank, whereby during forming any excess material can spread laterally outwardly to an extent permitted by the said cavity.

2. A method according to claim 1, wherein the blank is supported by a tube support with a clearance therebetween.

3. A method according to claim 1, wherein the pin has a length equal to the intended length of the said orifice and a distal surface, and the other tool on which the pin is not mounted, has a plunger with a distal face which, prior to forming, faces the distal face of the pin at a distance therefrom, and wherein during forming the said distal face of the pin and the said distal face of the plunger are brought into contact with one another.

4. A method according to claim 3, wherein the said plunger is spring-loaded, and the pin produces movement of plunger against the spring loading during moulding.

5. A method according to claim 3, wherein the extent of movement of the plunger is controlled by opposing faces which are formed thereon and which engage, in use, with abutment faces formed on the said other tool.

6. A method according to claim 1, wherein the pin is movably mounted in the one forming tool for movement towards and away from the other forming tool, and as the tools are brought together during moulding the distal end of the pin first engages the other forming tool and is then moved into the said one forming tool by the said other forming tool.

7. A method according to claim 6, wherein the pin is biassed by a biassing means towards the said other forming tool, the said engagement with the said other forming tool producing movement against the force of the biassing means.

8. A method according to claim 7, wherein the said biassing means is a compression spring.

9. A method according to claim 1, wherein the pin is on the inner forming tool.

10. A method according to claim 1, wherein the tools do not rotate during moulding.

11. A method according to claim 1, wherein the tools rotate in unison during moulding.

12. A method according to claim 1, wherein the said article is a body for a capsule adapted for use in a needleless injector.

13. A method according to claim 1, wherein the said article is a syringe body.

14. A method according to claim 1, wherein the formable material is glass.

15. A method according to claim 1, wherein the end region of the blank is brought into its condition to permit it to be formed, by heating.

16. A method according to claim 15, wherein the inner forming tool rotates during heating of the blank.

17. A method according to claim 15, wherein the inner forming tool does not rotate during heating of the blank.

18. An apparatus for making an article from a formable material, the article having a cavity communicating with the exterior via an orifice, the apparatus comprising an inner forming tool for receiving an open-ended blank, and an outer forming tool for engaging an end region of the blank adjacent to said open end to form the same, a first one of the said tools having a pin extending therefrom, and a second one of said tools comprising an other tool, said tools being so arranged that when they are brought together to form the said end region into a desired shape the inner surface of the said end region conforms to the adjacent surface of the inner forming tool, with the pin defining the said orifice, the outer forming tool having a cavity therein, facing the inner forming tool, of larger cross-section than the blank and extending beyond the outside of the blank, whereby during forming any excess material can spread laterally outwardly to an extent permitted by the said cavity.

19. An apparatus according to claim 18, wherein a tube support is provided for supporting the blank with a clearance therebetween.

20. An apparatus according to claim 18, wherein the pin has a length equal to the intended length of the said orifice and a distal surface, and the other tool, on which the pin is not mounted, has a plunger with a distal face which, prior to forming, faces the distal face of the pin at a distance therefrom, the apparatus further comprising means for bringing the said distal face of the pin and the said distal face of the plunger into contact with one another during forming.

21. An apparatus according to claim 20, wherein the said plunger is spring-loaded, and apparatus is so arranged that the pin produces movement of plunger against the spring loading during moulding.

22. An apparatus according to claim 20, wherein the extent of movement of the plunger is controlled by opposing faces which are formed thereon and which are engageable, in use, with abutment faces formed on the said other tool.

23. An apparatus according to claim 18, wherein the pin is movably mounted in the one forming tool for movement towards and away from the other forming tool, whereby, in use, as the tools are brought together during moulding the distal end of the pin first engages the other forming tool and is then moved into the one forming tool by the other forming tool.

24. An apparatus according to claim 23, wherein the pin is biassed by a biassing means towards the other forming tool, the said engagement with the other forming tool producing movement, in use, against the force of the biassing means.

25. An apparatus according to claim 24, wherein the said biassing means is a compression spring.

26. An apparatus according to claim 18, wherein the pin is on the inner forming tool.

27. An apparatus according to claim 18, comprising means for heating the said end region of the blank to bring it into a condition to permit it to be moulded.

28. An apparatus according to any one of claims 18, comprising means for rotating the inner forming tool.

29. An apparatus according to claim 28, comprising means for rotating the outer forming tool.

* * * * *